United States Patent
Klisch

(10) Patent No.: US 7,585,318 B2
(45) Date of Patent: Sep. 8, 2009

(54) MEDICAL DEVICES AND METHODS OF MAKING THE SAME

(75) Inventor: Leo M. Klisch, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 959 days.

(21) Appl. No.: 10/871,443

(22) Filed: Jun. 18, 2004

(65) Prior Publication Data

US 2005/0283225 A1    Dec. 22, 2005

(51) Int. Cl.
*A61F 2/06* (2006.01)

(52) U.S. Cl. .................................... 623/1.15

(58) Field of Classification Search ............... 623/1.1, 623/1.15, 1.39, 1.42; 606/191–198; 219/121.11–121.4; 204/192.15, 192, 14, 192.21–192.24; 128/898
See application file for complete search history.

(56) References Cited

U.S. PATENT DOCUMENTS

| | | | |
|---|---|---|---|
| 3,999,028 A | 12/1976 | Saito et al. ................. 219/69 |
| 4,958,625 A | 9/1990 | Bates et al. ................ 128/754 |
| 5,073,694 A | 12/1991 | Tessier et al. ........... 219/121.7 |
| 5,090,419 A | 2/1992 | Palestrant .................. 128/754 |
| 5,195,969 A | 3/1993 | Wang et al. .................. 604/96 |
| 5,270,086 A | 12/1993 | Hamlin ..................... 428/35.2 |
| 5,366,504 A | 11/1994 | Andersen et al. ............. 623/11 |
| 5,368,045 A | 11/1994 | Clement et al. ............ 128/754 |
| 5,674,242 A | 10/1997 | Phan et al. ................. 606/198 |
| 5,725,547 A | 3/1998 | Chuter ....................... 606/194 |
| 5,741,333 A | 4/1998 | Frid ............................ 623/12 |
| 5,994,667 A | 11/1999 | Merdan et al. .......... 219/121.67 |
| 6,027,526 A | 2/2000 | Limon et al. ................... 623/1 |
| 6,096,175 A * | 8/2000 | Roth ..................... 204/192.15 |
| 6,146,404 A | 11/2000 | Kim et al. .................. 606/200 |
| 6,159,237 A | 12/2000 | Alt et al. ................... 623/1.11 |
| 6,171,327 B1 | 1/2001 | Daniel ........................ 606/200 |
| 6,190,404 B1 | 2/2001 | Palmaz et al. .............. 623/1.15 |
| 6,264,690 B1 | 7/2001 | Von Oepen ................... 623/1.3 |
| 6,287,335 B1 | 9/2001 | Drasler et al. ............. 623/1.28 |
| 6,342,062 B1 | 1/2002 | Suon et al. .................. 606/200 |
| 6,379,383 B1 | 4/2002 | Palmaz et al. .............. 623/1.49 |
| 6,537,310 B1 | 3/2003 | Palmaz et al. .............. 623/1.13 |
| 6,563,080 B2 | 5/2003 | Shapovalov et al. .... 219/121.72 |
| 6,676,987 B2 | 1/2004 | Zhong et al. ............... 627/2.24 |
| 6,913,617 B1 * | 7/2005 | Reiss ......................... 623/1.15 |

(Continued)

FOREIGN PATENT DOCUMENTS

DE    19628879    4/1999

(Continued)

OTHER PUBLICATIONS

Schetsky, L. McDonald, Shaper Memory Alloys, Encyclopedia of Chemical Technology (3rd ed.), John Wiley & Sons, 1982, col. 20, pp. 726-736.

(Continued)

*Primary Examiner*—Kevin T Truong
(74) *Attorney, Agent, or Firm*—Vidas, Arrett & Steinkraus

(57) ABSTRACT

A method of making a medical device includes positioning a tool within a lumen of an elongated workpiece and discharging electric current across a gap between the tool and the workpiece to remove a portion of the workpiece.

4 Claims, 15 Drawing Sheets

U.S. PATENT DOCUMENTS

| | | | |
|---|---|---|---|
| 2002/0010504 A1 | 1/2002 | Alt | 623/1.15 |
| 2002/0017503 A1 | 2/2002 | Banas et al. | 219/69.11 |
| 2002/0179573 A1 | 12/2002 | Gianchandani et al. | 219/69.11 |
| 2003/0024534 A1 | 2/2003 | Silvestri et al. | 128/846 |
| 2003/0185895 A1 | 10/2003 | Lanphere et al. | 424/493 |

FOREIGN PATENT DOCUMENTS

| | | |
|---|---|---|
| EP | 0916362 | 5/1999 |
| WO | WO 02/071975 | 9/2002 |

OTHER PUBLICATIONS

U.S. Appl. No. 10/390,202, filed Mar. 17, 2003, Zhong et al.

* cited by examiner

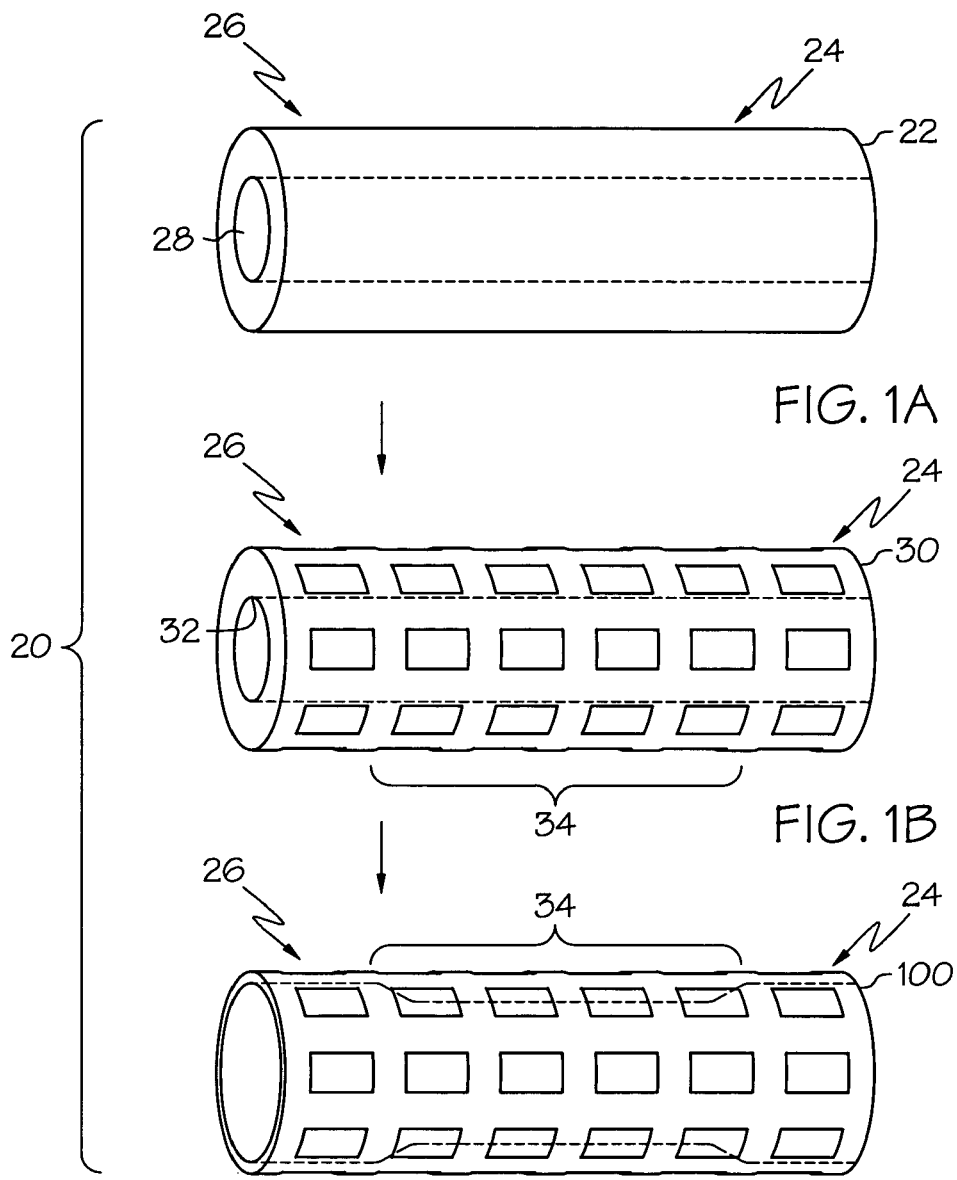
FIG. 1A
FIG. 1B
FIG. 1C
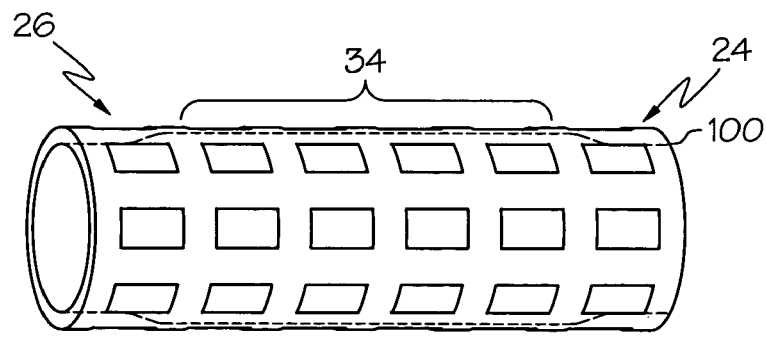
FIG. 1D

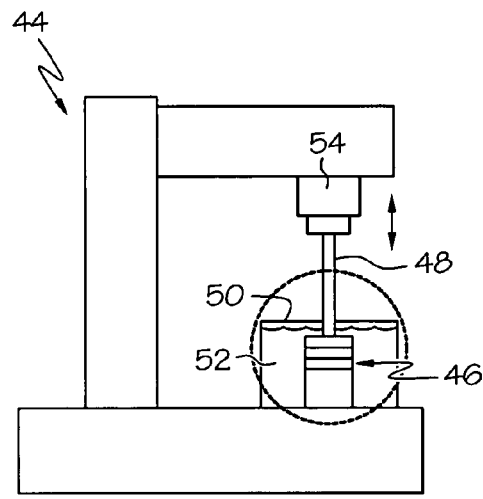
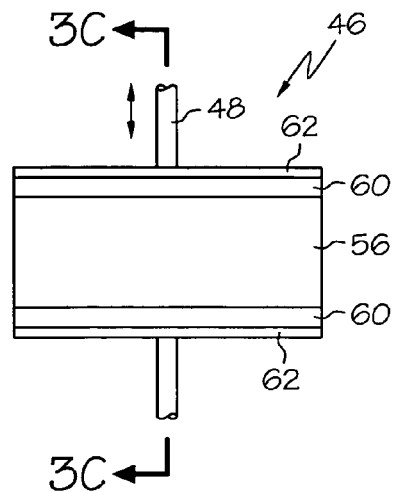
FIG. 3A　　　　　　　FIG. 3B
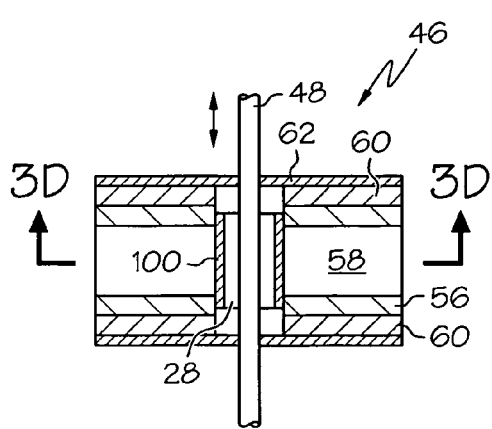
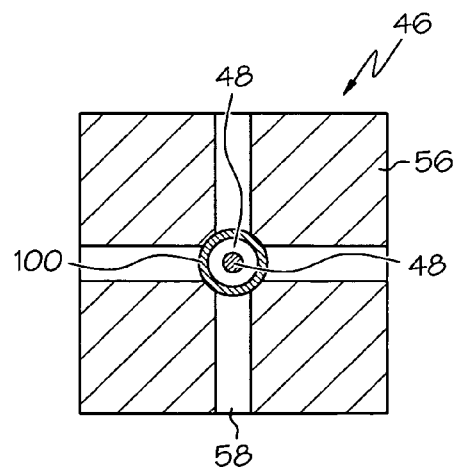
FIG. 3C　　　　　　　FIG. 3D

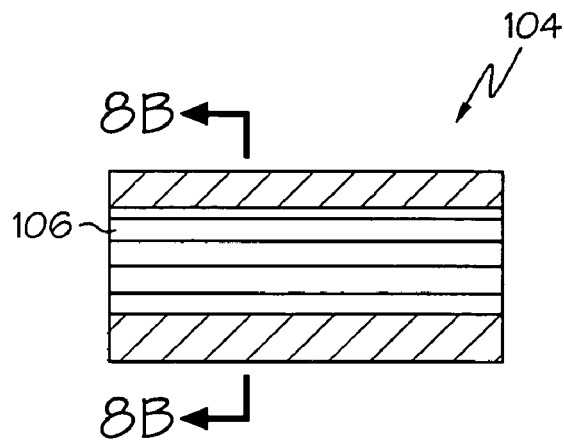
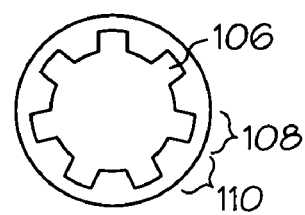
FIG. 8A
FIG. 8B
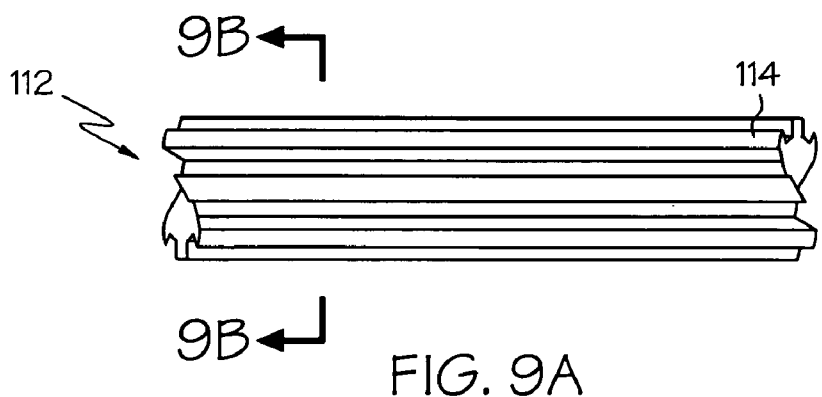
FIG. 9A
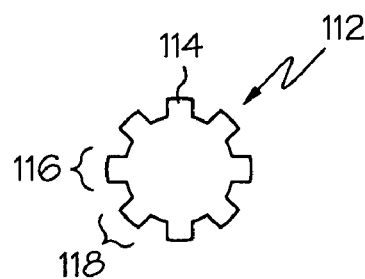
FIG. 9B

MEDICAL DEVICES AND METHODS OF MAKING THE SAME

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents and covered stents, sometimes called 'stent -grafts'.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

In one delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self expand by its own internal elastic restoring force.

In another technique, the expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In some cases, a balloon catheter includes a hypotube. The hypotube is often designed to act as a part of the conduit for the inflation fluid and to impart an appropriate amount of stiffness to the balloon catheter so that the balloon catheter can be positioned (e.g., in a blood vessel) within a patient.

All US patents and applications and all other published documents mentioned anywhere in this disclosure are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

SUMMARY

In one aspect, the invention is directed to a method of making a medical device, the method comprising positioning a tool within a lumen of an elongated workpiece and discharging electric current across a gap between the tool and the workpiece to remove a portion of the workpiece.

The invention is also directed to a method of making a tool, the method comprising positioning a workpiece through an aperture of a machining plate and discharging electric current across a gap between the machining plate and the workpiece to remove a portion of the workpiece.

The invention is further directed to a method of making a medical device, the method comprising positioning a rod through an aperture of a machining plate, discharging electric current across a gap between the machining plate and the rod to remove a portion of the rod, positioning the rod within a lumen of an elongated workpiece, and discharging electric current across a gap between the tool and the workpiece to remove a portion of the workpiece.

The invention is also directed to an apparatus comprising a fixture and a power source. The fixture comprises a machining plate and a positioning plate. The positioning plate slidably receives the workpiece and positions the workpiece within an aperture of the machining plate. The positioning plate is electrically isolated from the machining plate by an insulator. The power source provides an open gap voltage between a workpiece and the machining plate. The machining plate is arranged and configured to remove material from the workpiece by discharging an electric current across a gap between the machining plate and the workpiece.

The invention is further directed to a stent having a substantially constant outer diameter, a first region of the stent having a first wall thickness and a second region having a second wall thickness different than the first wall thickness.

The invention is also directed to a stent having an inner surface and an outer surface, the inner surface defining a lumen extending between first-and second ends of the stent, wherein the inner surface of the stent includes a first region and a stepped region having an internal diameter greater than an internal diameter of the first region.

The invention is further directed to a stent having an inner surface and an outer surface, the inner surface defining a lumen-extending between first and second ends of the stent, wherein the inner surface has a region of variable inner diameter.

The invention is also directed to an apparatus for machining a workpiece comprising a fixture, a machining plate, an insulating plate and a power source. The fixture comprising stacked plates including a machining plate having a first opening extending between broad surfaces of the machining plate, an insulating plate having a second opening extending therethrough, the insulating plate positioned between the machining plate and a positioning plate, the positioning plate including a third opening extending between broad surfaces of the positioning plate, and a power source for generating an open gap voltage between the machining plate and the workpiece. The third opening is arranged and configured to position the workpiece within the first opening of the machining plate. A portion of the workpiece within the first aperture of the machining plate discharges an electric current across a gap between the machining plate and the workpiece.

The invention is also directed to an apparatus for machining an inner surface of a stent, the inner surface defining a lumen extending between ends of the stent. The apparatus comprises a fixture comprising stacked plates. The fixture includes a mount for releasably positioning a stent within the fixture, the mount including a channel for flushing fluid over a surface of the stent. The fixture also includes an insulating plate positioned between the mount and a positioning plate, the insulating plate having a first opening for receiving a tool and corresponding with the channel of the stent, the positioning plate having a second opening arranged and configured to position the tool within the first opening of the insulating plate and within the channel of the stent. The fixture further includes a power source for generating an open gap voltage between the tool and the stent. A portion of the tool within the channel of the stent discharges an electric current across a gap between the tool and the stent.

The invention is also directed to a method of forming a tool using any of the inventive apparatuses disclosed herein.

Additional details and/or embodiments of the invention are discussed below.

DESCRIPTION OF DRAWINGS

FIGS. 1A, 1B, and 1C illustrate a method of making a medical device.

FIG. 1D illustrates a stent whose middle portion has been thinned relative to the ends.

FIG. 3A illustrates an electrical machining apparatus; FIG. 3B is a side view of a fixture of the apparatus of FIG. 3A; FIG. 3C is a cross-sectional view of the fixture of FIG. 3B, taken along line 3C-3C; and FIG. 3D is a cross-sectional view of the fixture of FIG. 3C, taken along line 3D-3D.

FIG. 8A is a cross-sectional view of a stent; and FIG. 8B is a cross-sectional view of the stent of FIG. 8A, taken along line 8B-8B.

FIG. 9A is an illustration of a tool; and FIG. 9B is a cross-sectional view of the tool of FIG. 9A, taken along line 9B-9B.

DETAILED DESCRIPTION

Figure 2A:
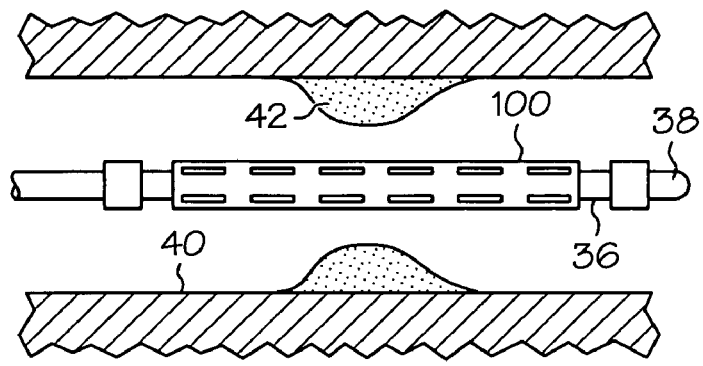
FIGS. 2A, 2B, and 2C illustrate a method of delivering a stent.

Referring to FIGS. 1A-1C, a method 20 of making a medical device (as shown, a stent 100) is shown. Method 20 includes providing an elongated member 22 (such as a tube) having a first end portion 24, a second end portion 26, and a lumen 28 extending between the end portions (FIG. 1A). Elongated member 22 is then formed into an intermediate member 30, for example, by laser cutting (FIG. 1B) techniques as described, for example, in U.S. Pat. No. 5,994,667, U.S. Pat. No. 6,563,080 and U.S. Pat. No. 5,073,694. Next, selected portions of intermediate member 30 are removed to form stent 100 using an electrical machining process described in detail below. As shown, selected portions of the inner surface 32 of intermediate member 30 are removed such that end portions 24 and 26 are relatively thinner than a portion 34 between the end portions. The thinness of end portions 24 and 26 allow them to be easily deformed (e.g., flexed) during use, thereby enhancing securement of stent 100 during use.

Referring to FIG. 1D, a stent can also be made in which selected portions of the inner surface 32 of intermediate member 30 are removed such that end portions 24 and 26 are relatively thicker than a portion 34 between the end portions. The thinness of portion 34 allows for a deflated or uninflated balloon to expand slightly into this recessed area for better securement. This would also allow the center portion of the stent to expand first if that is the desired deployment mode for the stent. Thus, using the inventive method and apparatus, the center of the stent could be thinned without thinning the ends of the stent.

Figure 2B:
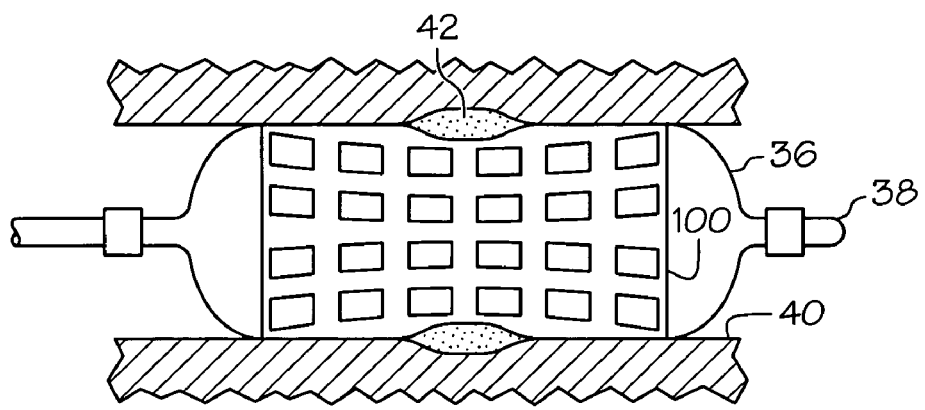
Figure 2C:
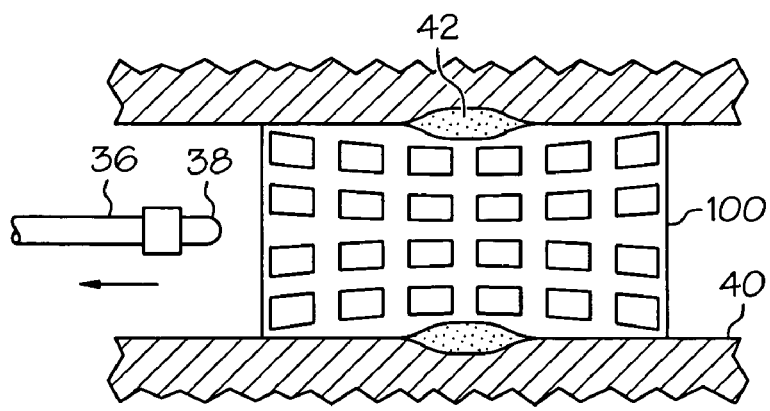

Referring to FIGS. 2A-2C, the delivery of stent 100 is illustrated. Stent 100 is carried by a balloon 36 (such as a compliant balloon) of a balloon catheter 38, and delivered through a vessel 40, as shown, one having a stenosis 42. At the target site, balloon 36 is inflated to radially expand stent 100, thereby widening the constriction caused by stenosis 42 and enhancing fluid flow through vessel 40. Since end portions 24 and 26 are relatively thin, they can be more easily expanded than portion 34. For example, as shown in FIG. 2B, end portions 24 and 26 can be expanded such that they flare outwardly to anchor stent 100 in position. Subsequently, balloon 36 is deflated, and catheter 38 is withdrawn (FIG. 2C).

As indicated above, during manufacture of stent 100, portions of intermediate member 30 are selectively removed to from a stent having variable wall thickness. The removal process involves electrical machining in which a workpiece (e.g., a stent) and a tool are used as electrodes, and an open gap voltage is generated between the workpiece and the tool. The voltage in turn generates a spark that can remove portions of the workpiece.

Referring now to FIG. 3A, a device 44 suitable for electrical machining includes a fixture 46 for holding a workpiece (one electrode) and a tool 48 (another electrode). Fixture 46 is positioned within a tank 50 containing a fluid 52. Tool 48 (such as a rod) is mounted on a movable member 54 (such as a ram, a quill, or a rotatable spindle) adapted to control the movement of the tool through fixture 46.

Referring to FIGS. 3B-3D, fixture 30 is a stationary assembly configured to receive and to secure a workpiece (as shown, stent 100) such that the workpiece can serve as an electrode. Fixture 46 includes an electrically-conducting (e.g., stainless steel) mount 56 (such as a plate having an opening to receive the workpiece) having flushing channels 58. Channels 5 & allow fluid 52 (described below) to circulate through and/or around the workpiece. On each side of mount 56, fixture 30 includes an insulator 60 and a positioning plate 62, all of which include an opening to receive tool 48. Positioning plate 62 is formed to position tool 48 within the lumen of the workpiece, e.g., spaced from the inner surface of the workpiece. Positioning plate 62 can be formed of a metal (such as stainless steel) to provide tight tolerance between tool 48 and the positioning plate, while allowing the tool to be translated and/or rotated and maintaining a spaced-apart relationship between the tool and the workpiece (e.g., stent 100). Insulator 60 electrically insulates positioning plate 62 from mount 56, and thus insulates tool 48 (which can contact the positioning plate) from the workpiece (which contacts the mount). Insulator 60 can be, for example, a polymer or ceramic plate, a polymer film, an adhesive resin, or a polymer tape. In other embodiments, positioning plate 62 is formed of an electrically insulating material (such as a ceramic) to eliminate the need for insulator 60. Alternatively or in addition, positioning plate 62 and mount 56 are spaced from each other to electrically insulate them.

Tool 48 is configured to be an electrode sized to be positioned within the workpiece (e.g., the lumen of stent 100). Tool 48 is also dimensioned to create a predetermined gap between the workpiece and the tool. Tool 48 can have one or more sections of constant dimension and/or one or more sections of varying dimension. In some embodiments, tool 48 has one or more longitudinally and/or circumferentially extending grooves and/or ridges. As described below, the shape of tool 48 can correspond to a shape that is to be produced in workpiece.

Tool 48, as well as mount 56 or positioning plate 62, can be formed of any suitable electrically conductive material, e.g., copper, brass, copper-tungsten, aluminum, stainless steel, 70/30 zinc tin, or graphite, including EDM-AIFS, available from Poco Graphite Inc. (Decatur, Tex.).

Fluid 52 is used for multiple purposes. Fluid 52 can serve, at least in part, as insulation between tool 48 and the workpiece, as a conductor, as a coolant, and as a flushing medium to remove material as the workpiece is machined. For example, fluid 52 can ionize to provide a spark channel and deionize to become an insulator. Fluid 52 can include a dielectric fluid, such as dielectric oil, kerosene, or water, e.g., deionized water. Fluid 52 can include an electrolyte, such as highly conductive solutions of inorganic salts, e.g., NaCl, KCl, and NaNO3. During use, fluid 52 can be circulated through channels 58, e.g., by employing a pump, or the fluid can be relatively stagnant. In some embodiments, particles (e.g., metals such as Au, Cu, Pt, Al, Cr or any other metal capable of bring plated to the stent) can be suspended in fluid 52. In some cases, the suspended particles can bond to the workpiece during discharge of the spark.

During use, tool 48 is positioned within the workpiece, and the tool and the workpiece are oppositely charged. The workpiece can be positively or negatively charged by charging mount 56, which is electrically insulated from tool 48. The charging generates an open gap voltage between the workpiece and tool 48, and the voltage produces a spark capable of removing material from the workpiece. During operation, tool 48 can be moved, e.g., translated, rotated, and/or vibrated. Movement of the tool relative to the stent allows for new electrode material to be presented, given that material is also removed from the tool. If needed, a second, finishing electrode may be used to complete the machining. For example, 90 percent of the removal can be effectuated with a first electrode and the remaining 10 percent completed with a second electrode.

Figure 4A:
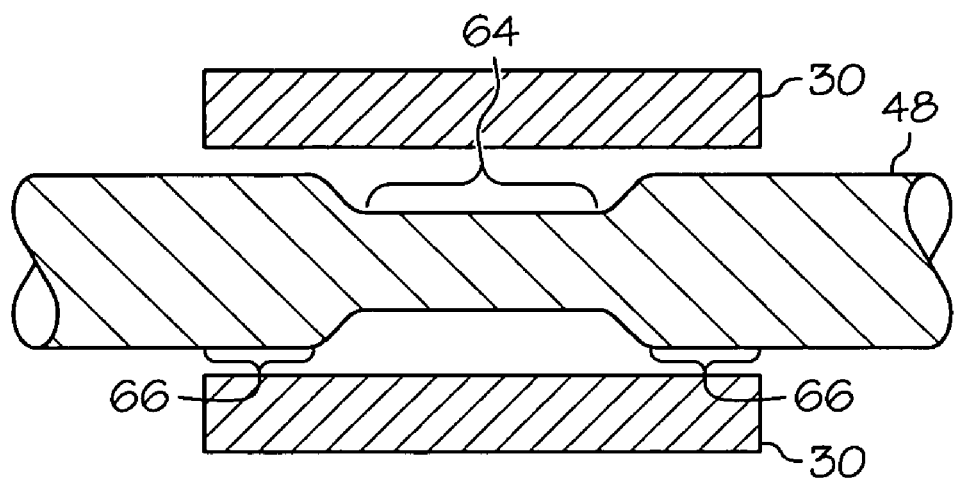
FIGS. 4A and 4B are cross-sectional views of a workpiece and a tool.
Figure 4B:
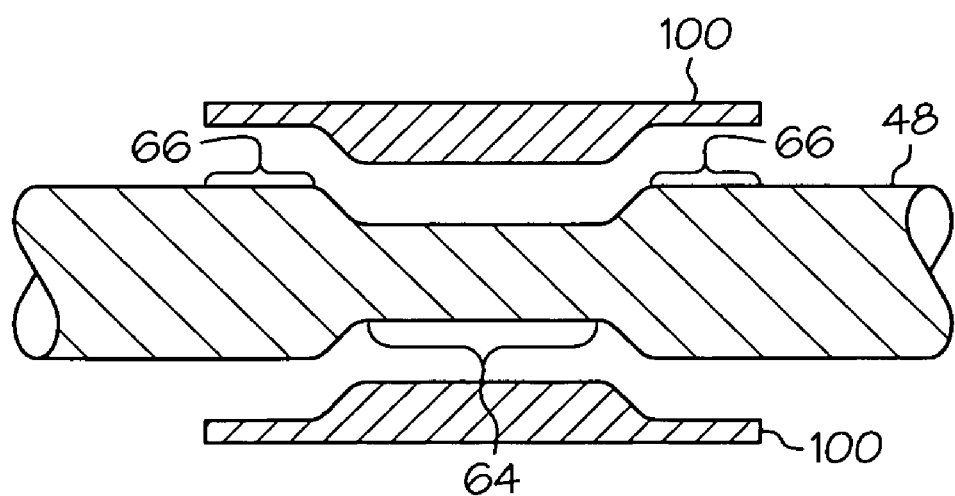

In particular, as indicated above, the shape of tool 48 can be selected to form a selected shape in the workpiece. For example, to form stent 100 having relatively thin end portions 24 and 26 such that the stent has an hourglass-like longitudinal cross section, a tool having the same profile can be used. Referring to FIGS. 4A and 4B, tool 48 has a narrowed portion 64 between relatively wider portions 66. As a result, wider portions 66 are closer to stent 100 than portion 64 is to the stent. In some cases, the distance between tool 48 and the workpiece, or the discharge gap, is less than 0.01 inch, such as less than 0.005, 0.001, or 0.0005 inch. When a predetermined voltage is applied across the discharge gap, a discharge spark is generated to remove material from stent 100. Since portions 66 are closer to stent 100 than portion 64, more material on the stent adjacent to portions 66 is removed than stent material adjacent to portion 64, consequently forming a stent with relatively thin end portions. In some cases, as stent material is removed adjacent to sections 66, the discharge gap increases to a point where spark discharges from sections 64 cease while discharges from section 66 continue. In some embodiments, sparks are discharged only within enlarged sections 66. In some embodiments, tool 48 is rotated, translated, and/or vibrated within the workpiece during discharge to reduce any effects from variations in the shape of the tool to provide a more consistent, evenly machined surface. Rotation and/or translation can also be used to present new electrode material and potentially put complex machined patterns into the sent ID wall with a simplified electrode shape.

Machining using an open gap voltage are exemplified by techniques such as electrical discharge machining ("EDM") and electrical chemical machining ("ECM"). An example of a suitable EDM apparatus is a Charmilles D10, available from Charmilles Corp., in Lincolnshire, Ill. A suitable power source is an Isopulse P25 also available from Charmilles Corp. EDM and ECM techniques and parameters are described, for example, in U.S. Pat. No. 3,999,028.

Figure 5A:
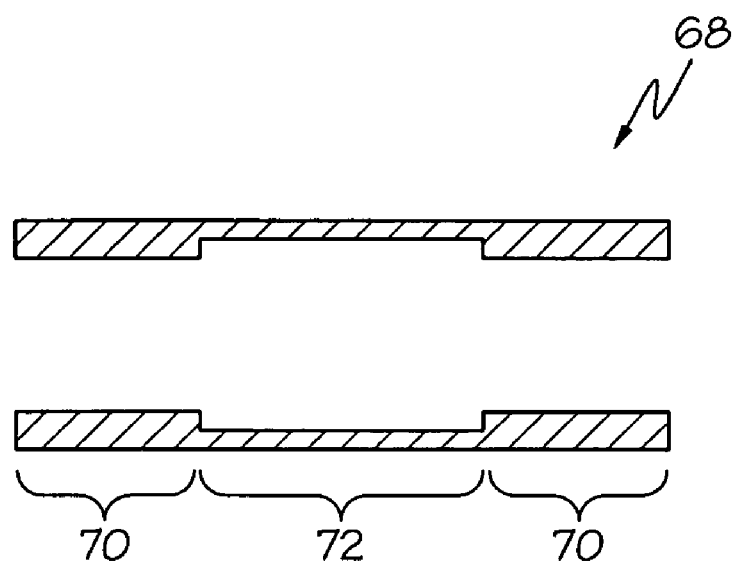
FIG. 5A is a cross-sectional view of a stent.
Figure 5B:
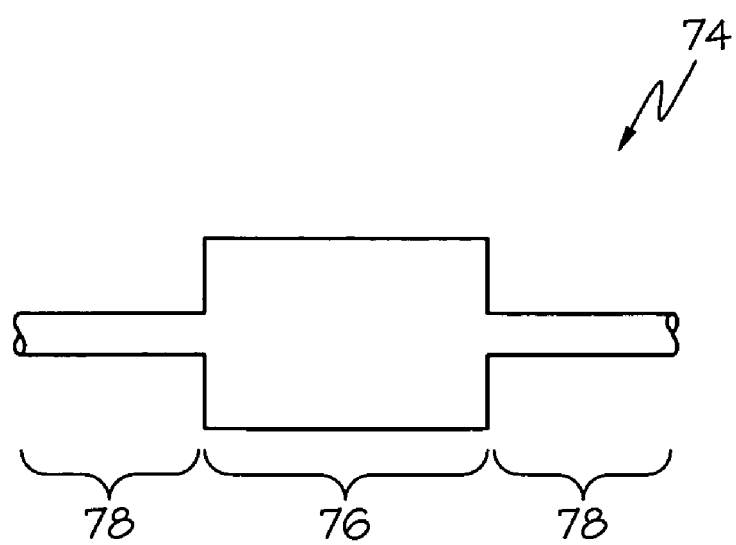
FIG. 5B is a cross-sectional view of a tool.

Other embodiments of stents having machined inner surfaces are possible. For example, FIGS. 5A, 5B, 6A, 6B, 7A, and 7B illustrate various embodiments of stents along with tools suitable to form the stents. Referring to FIGS. 5A and 5B, a stent 68 includes relatively thick end portions 70 and a relatively thin portion 72 between the end portions. Within each portion 70 and 72, the thickness is substantially constant. As shown, the change in thickness (and thus the diameter of the lumen of the stent) from portion 72 to portions 70 is abrupt (e.g., forming a stepped inner surface), vis-à-vis the relatively smooth transition shown in stent 100 (FIG. 4B). FIG. 5B shows an example of a tool 74 that can be used to form stent 68. Tool 74, having a cross-sectional profile similar to that of stent 68, includes an enlarged region 76 between relatively narrowed regions 78.

Figure 6A:
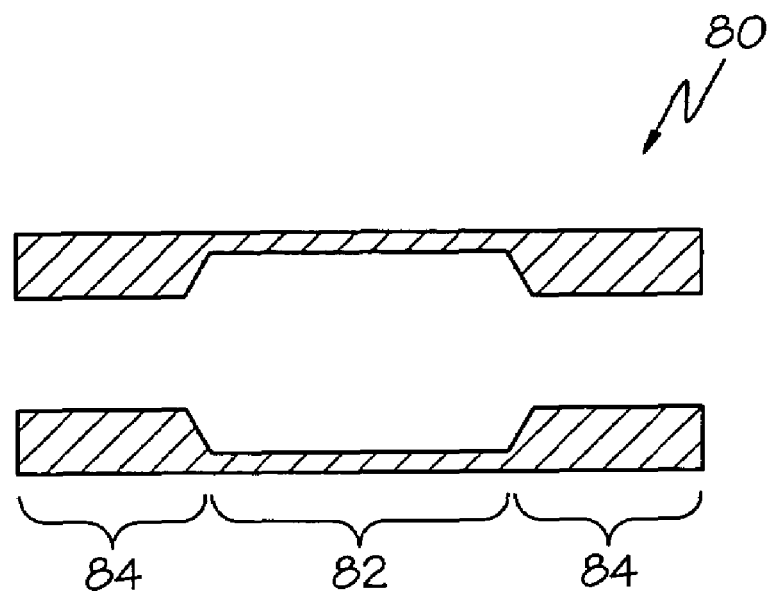
FIG. 6A is a cross-sectional view of a stent.
Figure 6B:
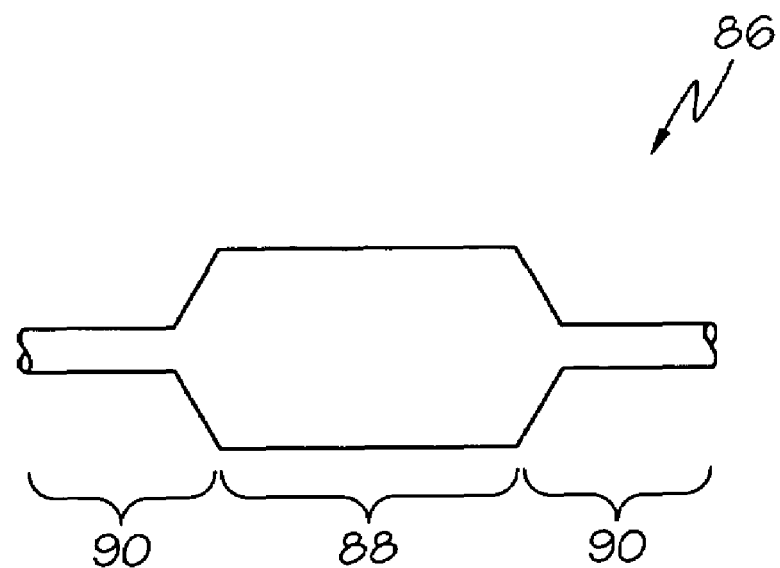
FIG. 6B is a cross-sectional view of a tool.

FIG. 6A shows another stent 80 having a relatively thin portion 82 between relatively thick end portions 84. The inner surface of stent 80 tapers between portion 82 and portions 84. FIG. 6B shows an example of a tool 86 that can be used to form stent 80. Tool 86 has an outer dimension that tapers from a region 88 of maximum width to regions 90 of lesser width. Desirably, the tool has a maximum outer dimension of less than about 20 mm.

Figure 7A:
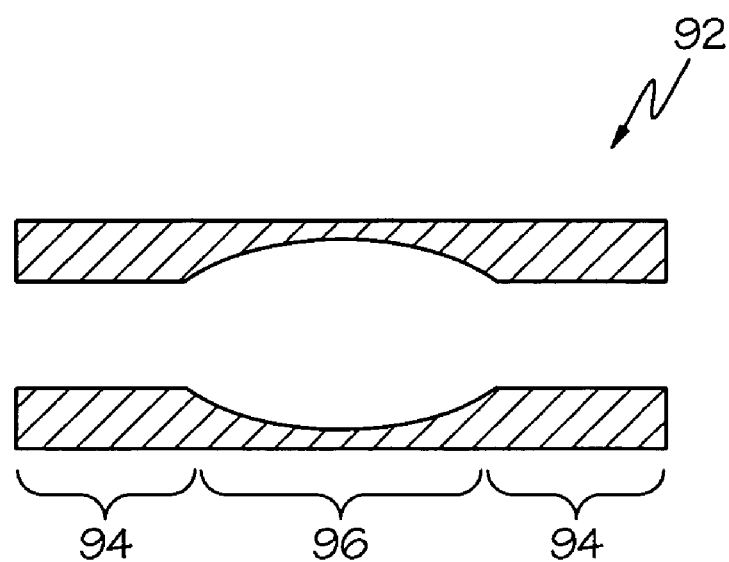
FIG. 7A is a cross-sectional view of a stent.
Figure 7B:
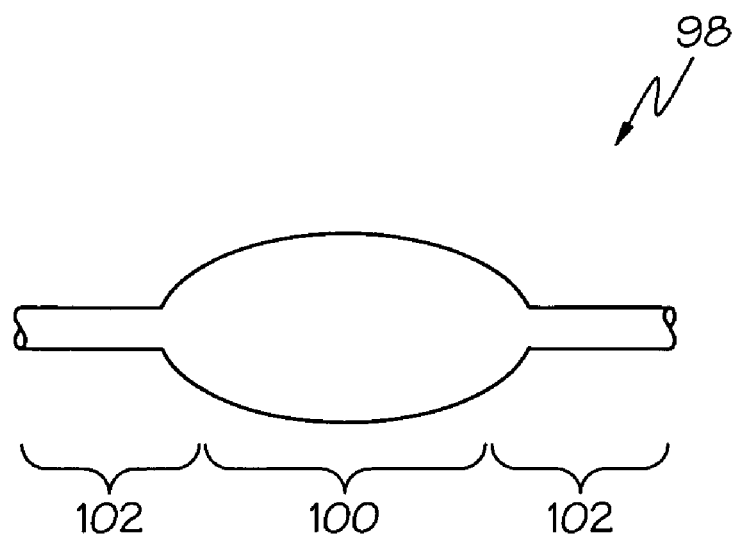
FIG. 7B is a cross-sectional view of a tool.

FIG. 7A shows yet another stent 92 having different wall thickness. Stent 92 includes regions 94 having relatively constant wall thickness along the length of the stent, and a region 96 having varying wall thickness along the length of the stent. FIG. 7B shows an example of a tool 98 that can be used to form stent 92. Tool 98 includes an enlarged section 100 of variable outer diameter and regions 102 of relatively constant outer dimension on both ends of section 100. Stents 68, 80, and 92 can be used, for example, to easily expand the middle portions of the stent. In other embodiments, the inner surface includes a combination of a step, a taper, and/or a varying thickness region, in any combination.

The electrical machining process described above can be used to form other features on a workpiece, such as on the inner surface of a stent. For example, a stent can include texturing, such as grooves, on a surface to enhance adhesion of the stent to another material, e.g., a polymer liner or graft. The texturing can increase the surface area of the stent, which can increase the amount of a drug that the stent can carry. Referring to FIGS. 8A and 8B, a stent 104 includes stepped, squared grooves 106 that extend longitudinally along the length of the stent. Grooves 106 form regions 108 in stent 104 having a wall thickness less than the wall thickness of region 110. FIGS. 9A and 9B show a tool 112 suitable for forming stent 104. Tool 112 includes squared ribs 114 extending longitudinally along the length and outwardly from a periphery of the tool. Ribs 114 can also be non-squared, such as rounded or tapered. Ribs 114 form regions 116 on tool 128 having a dimension (e.g., height) greater than a dimension of regions 118 of the tool. In some embodiments, ribs 114 extend only partially along the length of tool 128.

Figure 10:
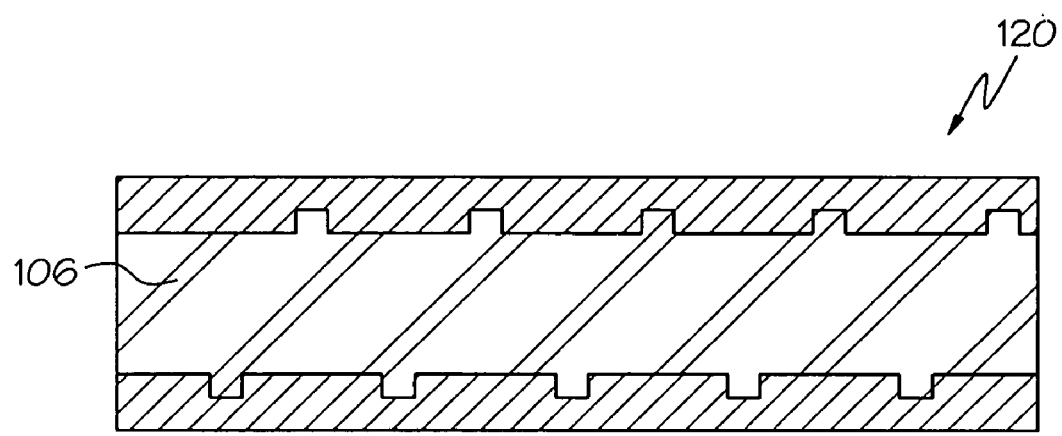
FIG. 10 is a cross-sectional view of a stent.
Figure 11:
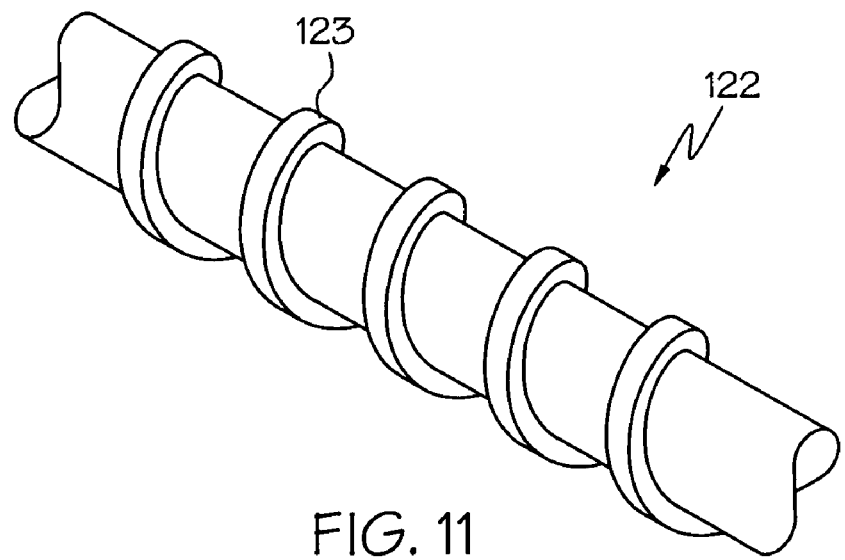
FIG. 11 is an illustration of a tool.
Figure 12:
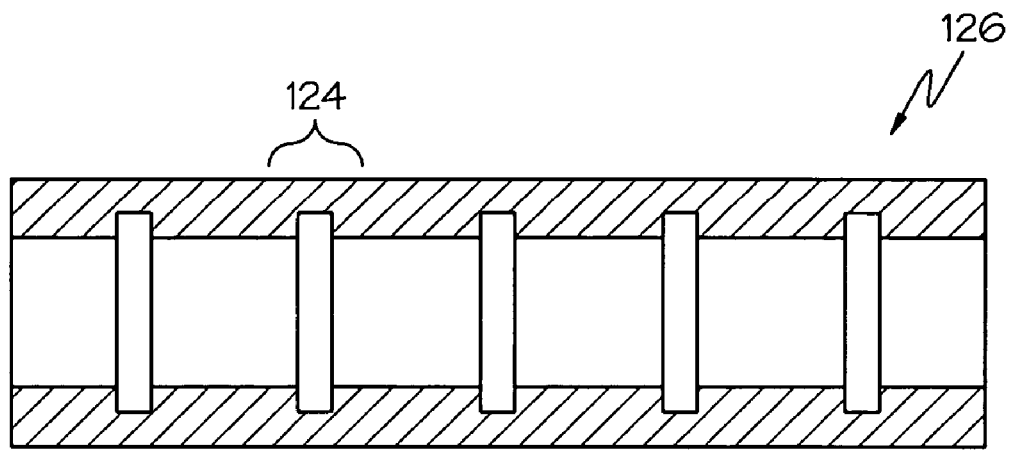
FIG. 12 is a cross-sectional view of a stent.
Figure 13:
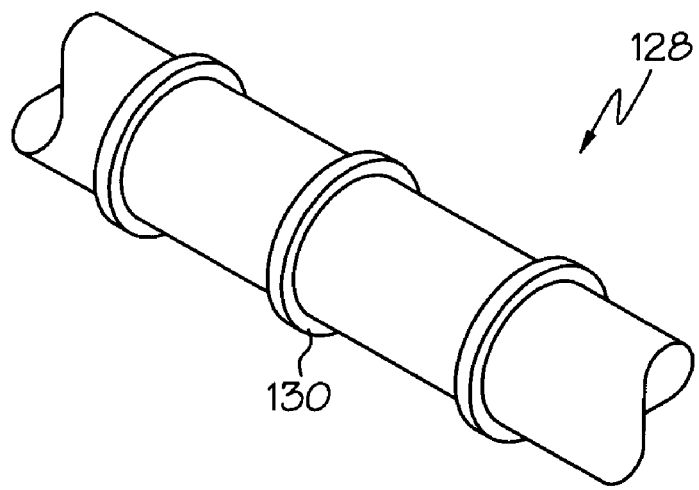
FIG. 13 is an illustration of a tool.

Other embodiments of stents having grooves are possible. For examples, grooves 106 can extend only partially along the length of the inner surface of stent 104. Non-parallel and/or intersecting grooves can be formed. In some cases, referring to FIG. 10, grooves 106 extend helically (e.g., spiral) around the inner surface of stent 120, e.g., by using a tool 122 having nonparallel and/or intersecting ribs 123 extend outwardly around the periphery of the tool FIG. 11). Or, ribs 123 can be formed by using a tool (e.g., a rod) having a protrusion, and translating and rotating the tool during manufacture. In some embodiments, referring to FIG. 12, grooves 124 extend transversely to the longitudinal axis of a stent 126. As shown in FIG. 13, a tool 128 having ribs 130 extending transversely to the longitudinal axis of the tool can be used. The grooves described above can have a cross section that tapers and/or is rounded. In other embodiments, the grooves can vary in dimension (e.g., width and/or depth) along the length of the stent.

Any combination of the above stent designs can be formed. For example, any of the stents described above having varying wall thickness can include one or more embodiments of grooves.

Generally, a stent formed by any of the above methods can be of any desired shape and size (e.g., coronary stents, aortic stents, peripheral vascular stents, gastrointestinal stents, urology stents, and neurology stents). Depending on the application, the stent can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., as described in U.S. Pat. No. 5,366,504).

A stent, or another workpiece, can be formed of any suitable electrically conductive material. Suitable stent materials that provide good mechanical properties and/or biocompatibility include, for example, stainless steel (e.g., 316L stainless steel), Nitinol (a nickel-titanium alloy), Elgiloy, L605 alloys, Ti-6Al-4V, and Co-28Cr-6Mo. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736.

The stent or workpiece can also include one or more radiopaque materials (e.g., layer(s)) to provide radiopacity and/or the radiopaque material(s) can be added to the stent material prior to machining the workpiece. Suitable radiopaque materials include metallic elements having atomic numbers greater than 26, e.g., greater than 43. In some cases, the materials have a density greater than about 9.9 g/cc. In certain embodiments, the radiopaque material is relatively absorptive of X-rays, e.g., having a linear attenuation coefficient of at least 25 cm1, e.g., at least 50 cm1, at 100 keV. Some radiopaque materials include tantalum, platinum, iridium, palladium, tungsten, gold, ruthenium, and rhenium. The radiopaque material can include an alloy, such as a binary, a ternary or more complex alloy, containing one or more elements listed above with one or more other elements such as iron, nickel, cobalt, or titanium. A mixture (e.g., a powder mixture) of radiopaque material(s) and structural material(s) can be delivered to and formed at selected portion(s) of the stent, e.g., at its relatively thick or thin end portions. The mixture can enhance radiopacity without adversely affecting the mechanical properties of the stent. In some cases, the radiopaque material does not contribute substantially to the mechanical properties of the stent, but by forming the radiopaque material with a microstructure similar to that of the structural material, the difference in properties and stress concentration (which can lead to shearing) can be reduced (e.g., minimized) to provide a homogeneous composite.

The stent or workpiece can include one or more materials visible by magnetic resonance imaging (MRI). Suitable MRI visible materials are described, in U.S. Ser. No. 10/390,202, filed Mar. 17, 2003, hereby incorporated by reference.

A stent formed by any the above methods can also be a part of a stent-graft. For example, the stent can include and/or be attached to a biocompatible, non-porous or semi-porous polymer matrix made of polytetrafluoroethylene (PTFE), expanded PTFE, polyethylene, urethane, or polypropylene. The endoprosthesis can include a releasable therapeutic agent, drug, or a pharmaceutically active compound, such as described in U.S. Pat. No. 5,674,242, U.S. Ser. No. 09/895, 415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. The therapeutic agent can be carried by the polymer matrix, which can be attached to the inner and/or outer surface of the stent.

In use, a stent formed by any of the above methods can be used, e.g., delivered and expanded, according to the type of stent. For example, a stent can be delivered using a balloon catheter system, or a delivery system having a shaft supporting a self expandable stent and a sheath constraining the stent. Suitable catheter systems are described in, for example, Wang U.S. Pat. No. 5,195,969, and Hamlin U.S. Pat. No. 5,270,086. Suitable stents and stent delivery are also exemplified by the Radius® or Symbiot® systems, available from Boston Scientific Scimed, Maple Grove, Minn.

In other embodiments, during processing, the workpiece is moved while the tool is stationary. Similar to fixture 46 described above, the fixture is configured to be positioned within a tank containing a fluid of an ECM or EDM apparatus. As the workpiece moves through the tool (e.g., a fixture), the workpiece is machined, e.g., by having material removed from the workpiece.

Figure 14:
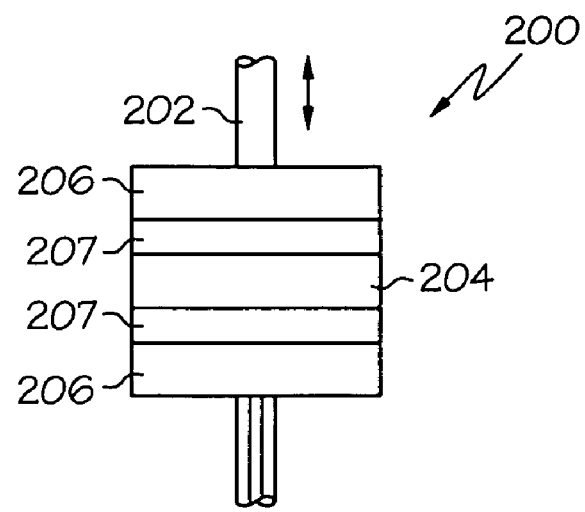
FIG. 14 is an illustration of a fixture and a workpiece.

Referring to FIG. 14, a fixture 200 for machining a workpiece 202 includes a machining plate 204, two positioning plates 206, and two insulators 207 that electrically isolate the positioning plates from the machining plate. Each of the plates have corresponding apertures to allow workpiece 202 to pass therethrough. Positioning plates 206 are formed to position workpiece 202 within the aperture of machining plate 204. Positioning plates 206 and their apertures allow for translational and/or rotational movement of workpiece 202 within the aperture of machining plate 204 while continuing to maintain a spaced-apart relationship between workpiece 202 and machining plate 204.

As indicated above, workpiece 202 is movable, e.g., relative to fixture 200. Workpiece 202 (e.g., a rod or a tube of any cross section) can be mounted on, e.g., a ram, a quill, or a rotating spindle. In some embodiments, workpiece 202 is translated at various speeds (e.g., less than about 1 inch per minute, such as 0.9, 0.8, 0.7, 0.6, 0.5, 0.4, 0.3, 0.2, 0.1 inch per minute or less) and/or the workpiece can move rotationally. As workpiece 202 moves through fixture 200, the workpiece is machined, e.g., by having material removed from the workpiece.

During a machining operation, workpiece 202 and machining plate 204 are oppositely charged. Machining plate 204 can be positively charged or negatively charged. Similar to the process described above, an open gap voltage is generated between workpiece 202 and machining plate 204. The open gap voltage is maintained by electrically isolating machining plate 204 from positioning plate 206 with insulator 207 (e.g., a plate, a film, a tape, or a resin), or by other methods described above. The voltage in turn produces an electrical discharge capable of machining workpiece 202, e.g., by selectively removing material from the workpiece. In some cases, a suitable amperage for, cutting is less than about 1 amp (e.g., about 0.5 amp).

Figure 15:
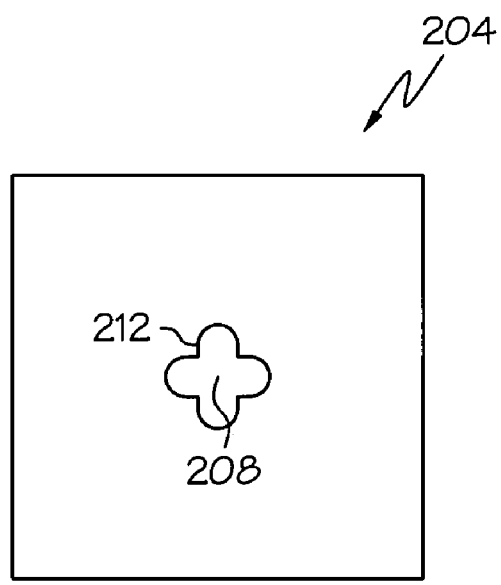
FIG. 15 is a plan view of a machining plate.
Figure 16:
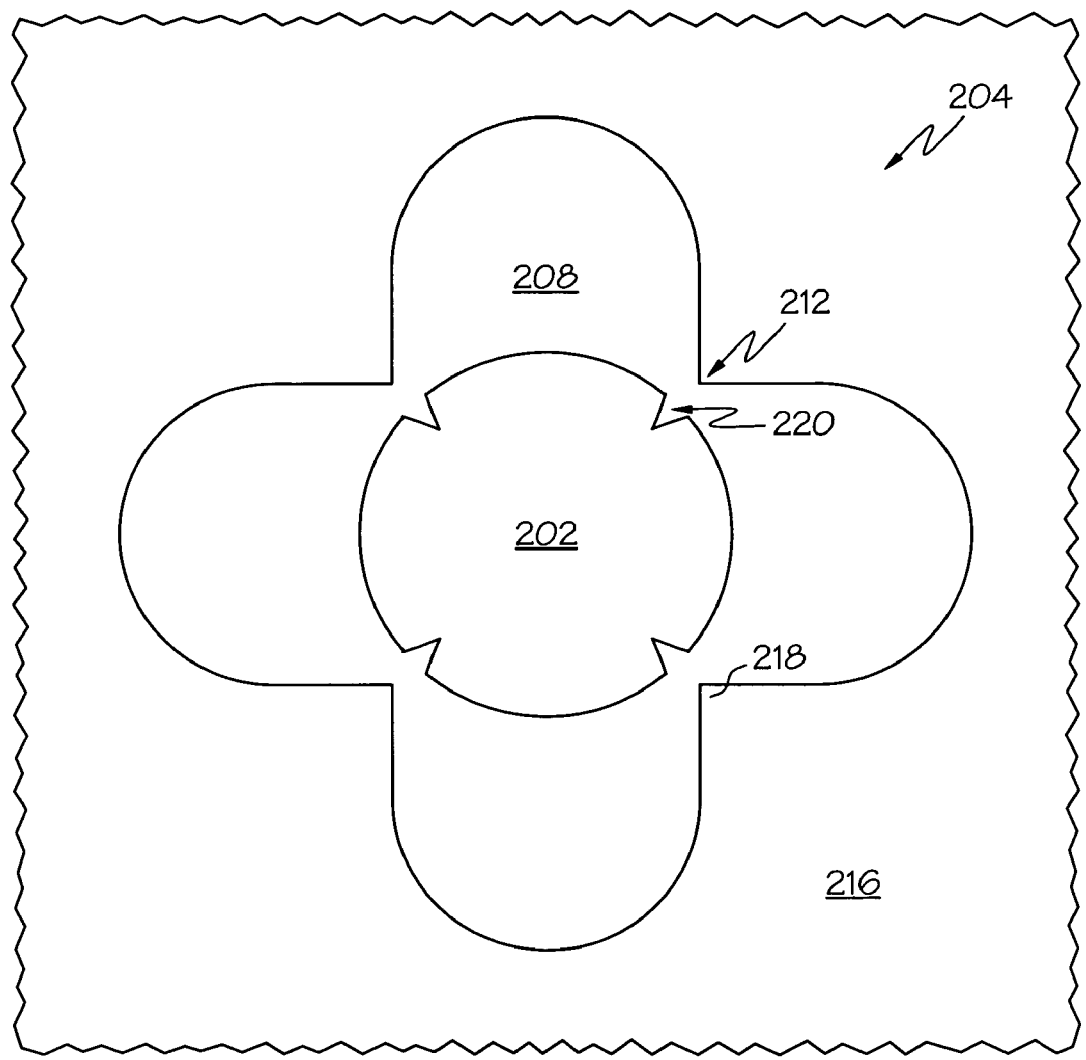
FIG. 16 is a detailed view of the machining plate of FIG. 15 and a workpiece.

For example, referring to FIG. 15, an embodiment of machining plate 204 includes aperture 208 having sections 212 of reduced dimension. Sections 212 provide a narrowed gap between workpiece 202 and machining plate 204. Referring to FIG. 16, as workpiece 202 is delivered through aperture 208, electrical discharge from sections 212 is capable of forming longitudinally extending grooves 220 into the workpiece. Depending on processing parameters, such as the feed speed of workpiece 202 and amperage, a greater amount of workpiece 202 can be removed adjacent tip 218. The amount of material removed can also be control by controlling the discharge gap; a lesser amount of material can be removed from workpiece 202 by increasing the gap. In some embodiments, workpiece 202 can be rotated and translated (e.g., unidirectionally or back and forth) to form grooves that extend helically about the longitudinal axis of the workpiece. Workpiece 202 can be rotated without any translational movement to form grooves that extend circumferentially around the workpiece, e.g., circular grooves.

The process described above can be used to make medical devices such as guidewires (e.g., a Meier steerable guide wire (for AAA stent procedure) and an ASAP Automated Biopsy System, e.g., described in U.S. Pat. Nos. 4,958,625, 5,368,045, and 5,090,419); filters (such as removable thrombus filters, e.g., described in U.S. Pat. No. 6,146,404, intravascular filters, e.g., described in U.S. Pat. No. 6,171,327, and vena cava filters, e.g., described in U.S. Pat. No. 6,342,062); markers bands, and catheter components such as hypotubes. The grooves can provide a textured (e.g., rough) surface that enhances securement of the workpiece to another component, such as a polymer tube around a hypotube. The process described above can be used to texture wires, which are then used to form a stent by knitting, weaving, or braiding. The textured wire can be securely attached to another material (such as a polymer layer) and/or be used to carry a drug.

Figure 17A:
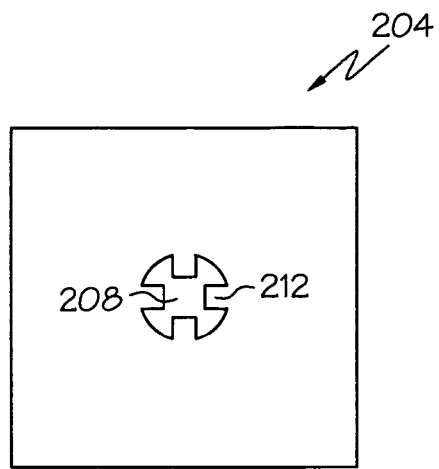
FIGS. 17A, 17B, and 17C are plan views of embodiments of machining plates.
Figure 17B:
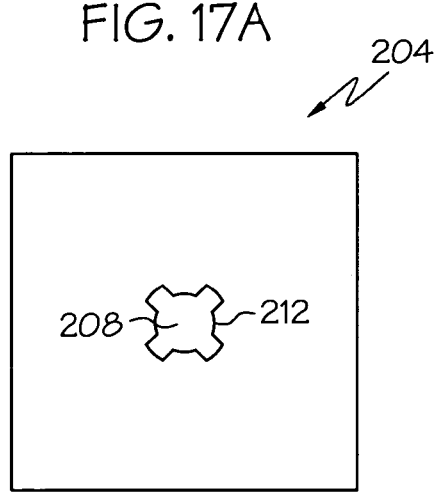
Figure 17C:
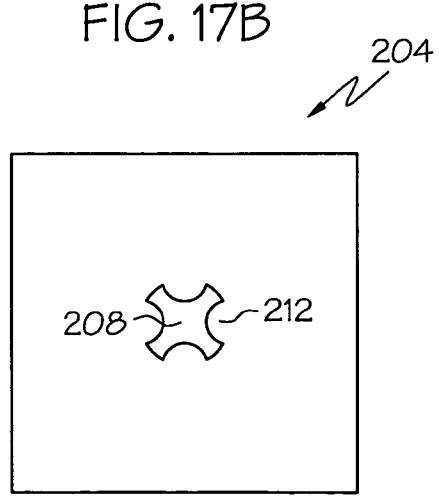

Other aperture contours can be used. For example, aperture 208 can have stepped sections 212 (FIG. 17A), tapered sections 212 (FIG. 17B), or rounded sections 212 (FIG. 17C). In some cases, the aperture can be contoured to provide a constant gap distance between machining plate 204 and workpiece 202.

Figure 18A:
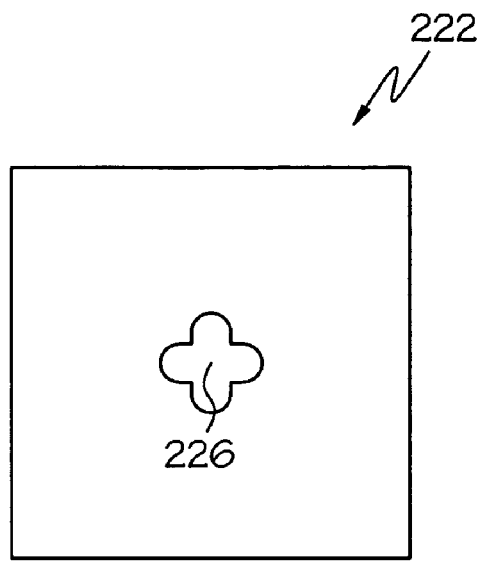
FIGS. 18A and 18B are plan view of embodiments of machining plates.
Figure 18B:
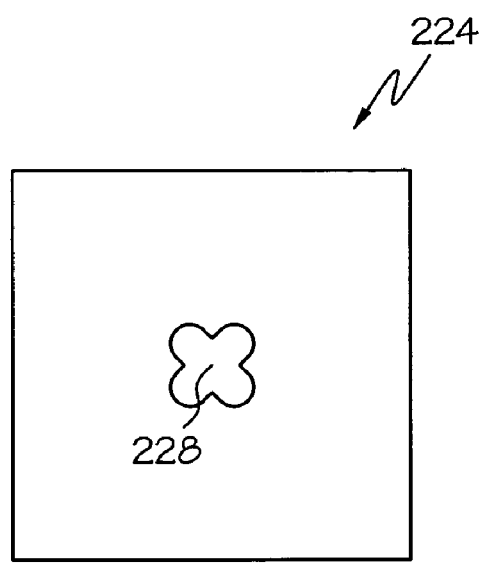

In some embodiments, more than one machining plate 204 is used to machine workpiece 202. Referring to FIGS. 18A and 18B, two machining plates 222 and 224 are illustrated having differing aperture contours. Machining plates 222, 224 can be stacked in one fixture to allow their respective apertures 226, 228 to machine selected portions of workpiece 202.

In embodiments where multiple machining plates are employed, the charge on each machining plate can be controlled individually or together. In some cases, as workpiece 202 passes through apertures of multiple machining plates, it may be desirable to machine only a discrete length of workpiece 202 with one machining plate. Where machining discrete lengths of an elongated workpiece is desirable, a relatively continuous machining process can be provided by controlling the charge of preselected ones of a series of machining plates.

The following example is illustrative and not intended to be limiting.

EXAMPLE

A tool (electrode) of desired design and a workpiece are provided. A work to electrode gap of 0.0001 V±0.0001 is established. The electrode plates are mounted into an EDM machine bath and submerged totally into dielectric fluid/oil. The workpiece is mounted into the head. The proper polarity is established with the workpiece having a negative voltage and the tool (electrode) having a positive voltage. The current is on for 5 second and turned off for 8 seconds. During the on time, the current is ½ amp where the maximum power setting is 3 amp. The head speed is controlled by the machine maintaining spark gap. Electrode flushing was not necessary. The bottom pilot plate was relieved so that the EDM burr would pass through the pilot hole—4 point contact. A POCO grade AF-5 graphite was used for the electrode material.

Figure 19:
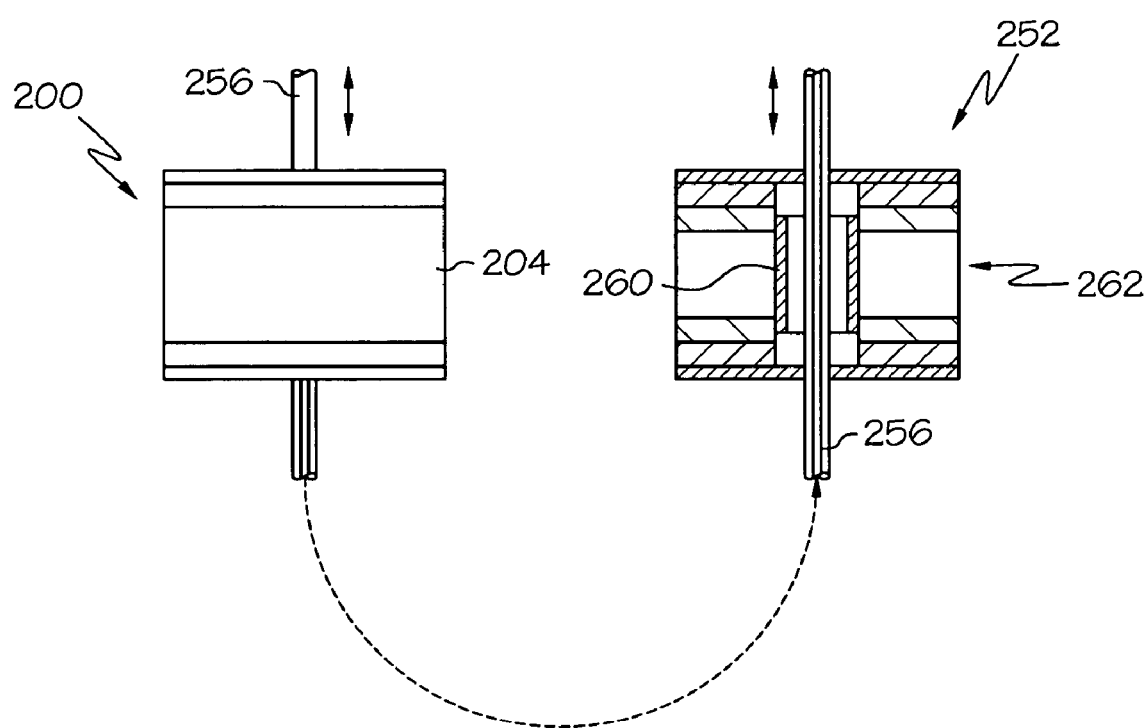
FIG. 19 are schematic illustrations of fixtures and workpieces.

In some cases, the methods described above can be combined. In general, the first apparatus would machine detail into the workpiece moving through the machining plate. The workpiece would then move in a continuous fashion into the next apparatus where it would machine detail into the stent inner diameter. For example, referring now to FIG. 19, a semi-continuous process is shown having multiple stations 250 and 252. Station 250 includes a fixture 200. An elongated workpiece 256 is machined at station 250 by passing workpiece 256 through a contoured aperture in machining plate 204. Workpiece 256 is then positioned within a lumen of a second workpiece 260 that is releasably positioned within fixture 46 at station 252. At this stage, workpiece 256 is the tool and is used to machine an inner surface of second workpiece 260. The inventive apparatuses and methods are not limited to two stations in sequence. Apparatuses and methods involving three or more stations, and more generally, a plurality of stations, are contemplated as well.

All of the features described herein may be combined in any combination. Each feature disclosed in this specification may be replaced by an alternative feature serving the same, equivalent, or similar purpose. Thus, unless expressly stated otherwise, each feature described is an example of a generic series of equivalent or similar features.

Other embodiments are within the claims.

What is claimed is:

1. An apparatus for machining a workpiece comprising:
   a fixture comprising stacked plates including a machining plate having a first opening extending between broad surfaces of the machining plate;
   an insulating plate having a second opening extending therethrough, the insulating plate positioned between the machining plate and a positioning plate, the positioning plate including a third opening extending between broad surfaces of the positioning plate; and a power source for generating an open gap voltage between the machining plate and the workpiece;

wherein the third opening is arranged and configured to position the workpiece within the first opening of the machining plate;

wherein a portion of the workpiece within the first opening of the machining plate discharges an electric current across a gap between the machining plate and the workpiece.

2. A method of forming a tool comprising:
providing the apparatus of claim 1;
selectively machining material from the workpiece by moving the workpiece longitudinally through the first aperture and discharging an electric current across the gap.

3. An apparatus for machining an inner surface of a stent, the inner surface defining a lumen extending between ends of the stent, the apparatus comprising:

a fixture comprising stacked plates, the fixture including a mount for releasably positioning a stent within the fixture, the mount including a channel for flushing fluid over a surface of the stent; an insulating plate positioned between the mount and a positioning plate, the insulating plate having a first opening for receiving a tool and corresponding with the channel of the stent, the positioning plate having a second opening arranged and configured to position the tool within the first opening of the insulating plate and within the channel of the stent; and a power source for generating an open gap voltage between the tool and the stent;

wherein a portion of the tool within the channel of the stent discharges an electric current across a gap between the tool and the stent.

4. A method of machining an inner surface of a stent, the method comprising:
providing the apparatus of claim 3;
positioning the tool within the second opening of the positioning plate; and
rotating the tool within the lumen of the stent.

* * * * *

UNITED STATES PATENT AND TRADEMARK OFFICE
CERTIFICATE OF CORRECTION

| | | |
|---|---|---|
| PATENT NO. | : 7,585,318 B2 | Page 1 of 1 |
| APPLICATION NO. | : 10/871443 | |
| DATED | : September 8, 2009 | |
| INVENTOR(S) | : Klisch | |

It is certified that error appears in the above-identified patent and that said Letters Patent is hereby corrected as shown below:

Title page, item (*) Notice: Delete "959 days" and insert --1482 days--.

Signed and Sealed this

Thirtieth Day of March, 2010

David J. Kappos
*Director of the United States Patent and Trademark Office*